United States Patent
Gennadios

(10) Patent No.: US 6,214,376 B1
(45) Date of Patent: Apr. 10, 2001

(54) NON-GELATIN SUBSTITUTES FOR ORAL DELIVERY CAPSULES, THEIR COMPOSITION AND PROCESS OF MANUFACTURE

(75) Inventor: Aristippos Gennadios, High Point, NC (US)

(73) Assignee: Banner Pharmacaps, Inc., High Point, NC (US)

( * ) Notice: Subject to any disclaimer, the term of this patent is extended or adjusted under 35 U.S.C. 154(b) by 0 days.

(21) Appl. No.: 09/140,758

(22) Filed: Aug. 25, 1998

(51) Int. Cl.$^7$ ............... A61K 9/48; A61K 9/64
(52) U.S. Cl. .......... 424/451; 424/452; 424/456
(58) Field of Search .................. 424/451, 452, 424/456

(56) References Cited

U.S. PATENT DOCUMENTS

| | | | |
|---|---|---|---|
| 3,956,173 | 5/1976 | Towle | 252/316 |
| 3,962,482 | 6/1976 | Comer et al. | 426/575 |
| 4,276,320 | 6/1981 | Moirano | 426/575 |
| 4,795,642 | * 1/1989 | Cohen et al. | 424/455 |
| 5,002,934 | 3/1991 | Norton et al. | 514/54 |
| 5,089,307 | * 2/1992 | Ninomiya et al. | 424/35.2 |
| 5,342,626 | * 8/1994 | Winston, Jr. et al. | 424/461 |
| 5,620,757 | 4/1997 | Ninomiya et al. | 428/34.8 |
| 5,756,123 | * 5/1998 | Yamamoto et al. | 424/451 |

OTHER PUBLICATIONS

*Food Product Design*, Hegenbart article "Bind for Glory: Designing Foods Using Gums," pp. 21, 24, 26, 29, 32, 35, 38, 42, Jan. 1993.

Chandrasekaran, R., et al., "Molecular architectures and functional properties of gellan gum and related polysaccharides", *Trends in Food Science & Technology*, vol. 6, pp. 153–148, (May 1995).

Hegenbart, S., "Understanding Carrageenan", *Food Product Design*, vol. 4(3), pp. 109–120, (Jun. 1994).

Sanders, G.R., et al., "Gellan Gum", *Food Technology*, pp. 63–70, (Apr. 1983).

\* cited by examiner

*Primary Examiner*—Thurman K. Page
*Assistant Examiner*—Todd D Ware
(74) *Attorney, Agent, or Firm*—Rhodes & Mason, P.L.L.C.

(57) ABSTRACT

Gelatin-free capsule for use in oral administration of medicines, cosmetic or bath applications, or dietary supplements can be prepared from compositions comprising a) 8–50% by weight of water-dispersible or water-soluble plasticizer, b) 0.5 to 12% by weight κ-carrageenan, c) 0 to 60% dextrins, and d) 1% to 95% by weight water, with the κ-carrageenan comprising at least 50% by weight of all gums forming or contributing to formation of thermoreversible gels in the composition. A capsule for oral administration or cosmetic application may comprise a fill material to be administered to a patient or subject and a capsule, the capsule comprising an aqueous based film comprising a) water-dispersible or water-soluble plasticizer, and b) carrageenan, with the carrageenan comprising at least 50% or 75% by weight of κ-carrageenan, and the carrageenan comprising at least 50% or 75% by weight of all gums which form or contribute to the formation of thermoreversible gels. A process for forming the capsules may comprise heating the composition, casting or extruding the composition into a film, gelling the composition by cooling, associating a fill material with the gelled composition (usually as a film) and sealing the film about the fill material.

53 Claims, No Drawings

NON-GELATIN SUBSTITUTES FOR ORAL DELIVERY CAPSULES, THEIR COMPOSITION AND PROCESS OF MANUFACTURE

BACKGROUND OF THE ART

1. Field of the Invention

The present invention relates to the field of binder and film-forming or gel-forming compositions, particularly towards substitutes for gelatin, and particularly for non-gelatin capsules for oral delivery of medications or diet supplements. Non-oral systems include cosmetics, bath additives, and the like.

2. Background of the Invention

Gelatin has found a wide range of commercial utility, and within certain industries is essentially irreplaceable. It has been used in wet processed photographic emulsions for more than a hundred years, it has been used to deliver pharmaceuticals in capsule form for more than one hundred years, it is used in cosmetics as a binder, and is regularly used in a wide range of food products, such as gelatin containing courses, compressed meats, pastries. It has many useful physical and chemical properties which support this broad range of utility.

Gelatin is manufactured by the hydrolysis of animal by-products which contain collagen. This is usually found in animal bones, animal skins and white animal connective tissue. The collagen containing material is boiled in water, leaving behind the colorless or pale yellow protein which constitutes the hydrophilic colloid material of the gelatin.

The primary sources of gelatin are from bovine animals and pigs, although fish and birds have been indicated in the literature as alternative, small volume sources of gelatin. The source of gelatin can be a problem for potential areas of use or for particular consumers. Large groups around the world cannot ingest any products of pigs (e.g., vegetarians, the Hebrews and the Muslims) or the products of beef (the Hindus and vegetarians). As medication and/or diet supplements are provided in gelatin capsules without any indication of the source of the gelatin, the use of capsules is restricted in areas where religious beliefs would need to question the source of the gelatin. Additionally, as there has recently been at least one alleged instance of cross-species contamination from cattle to humans (at least one alleged instance with bovine spongiform encephalopathy, BSE, or "Mad Cow Disease" in the United Kingdom), the use of uncontrolled by-products from animals has lost some level of commercial acceptance. It has become apparent that replacement compositions for gelatin which are not derived from animals are desirable.

Carrageenan is a natural hydrocolloid, a polysaccharide hydrocolloid, which is derived from seaweed. It comprises a carbohydrate polymer of repeating sugar units, which is linear, without significant numbers of branches or substitutions. Most, if not all, of the galactose units on a Carrageenan molecule possess a sulfate ester group. The exact position of the sulfate groups, the cations on the sulfate groups, and the possible presence of an anhydrous bridge on the molecule differentiates the various types of Carrageenan. There are basically three distinct types of Carrageenan which each behave differently and have distinct properties and differences. These are the kappa, iota and lambda forms of Carrageenan, although there are also minor fractions of mu and nu Carrageenan forms. These various forms can significantly vary in properties, as exemplified by the fact that lambda Carrageenan in solution is unable to associate into a structure, so that it cannot gel, but may act as a thickener. Both kappa and iota Carrageenan are able to gel. Kappa Carrageenan is known to form gels in the presence of potassium cations. These gels tend to be brittle and exhibit syneresis (contraction and release of entrapped liquid) as the gel shrinks. Iota Carrageenan tends to react strongly to calcium cations and forms a more tender, flexible gel than kappa Carrageenan that is not as susceptible to syneresis.

U.S. Pat. No. 3,962,482 describes clear, elastic, water gels and gel-forming compositions that are based on potassium-sensitive carrageenan in the form of an alkali metal or an ammonium salt and a water-soluble potassium salt. Addition to the composition of calcium-sensitive carrageenan, also in the form of an alkali metal or an ammonium salt, imparts freedom from syneresis. The water gels and the gel-forming compositions are characterized by essentially complete freedom from polyvalent metal cations. The invention is particularly concerned with the formation of compositions for use with edible dessert gels.

U.S. Pat. No. 5,089,307 discloses heat-sealable, edible films comprising at least a film layer containing a water-soluble polysaccharide as the principal component, or comprising at least (a) a film layer as described above and (b) a subfilm layer containing an alkali metal salt of casein, soybean protein or a combination of soybean protein and gelatin, as the principal component. Preferably, the water-soluble polysaccharide is composed chiefly of carrageenan and the film layer additionally contains a polyhydric alcohol. These edible films are useful in sealing or packaging powdery foods, granular foods, dry solid foods, oily foods and the like.

U.S. Pat. No. 5,002,934 describes aqueous gels, gel-forming compositions and composites containing the same, comprising carrageenan and a cation of such a type and in such a concentration that the gel has a transition midpoint temperature below 45° C. and a yield stress of at least 0.5 $kN/m^2$ at 5° C. The gels or gel-forming compositions can advantageously be used in food and toiletry products.

U.S. Pat. No. 4,276,320 describes a method and a kappa carrageenan composition for making a water dessert gel having a controlled melting temperature so as to soften or melt within the mouth of the consumer and providing for excellent flavor release, good mouth feel and containing only kappa carrageenan, and sodium salt of a sequestering agent with ionizable potassium in amounts sufficient to sequester all polyvalent cations present.

U.S. Pat. No. 3,956,173 describes cold water gellable compositions that are prepared based on the sodium salt of kappa-carrageenan and a potassium salt. Gelation is controlled so that good quality gels result by encapsulating the potassium salt in a water-soluble hydroxypropyl cellulose.

Each of these various systems has particular needs due to the specific types of use to which the Carrageenan compositions are put. There is no specific disclosure within these references as to the parameters and modifications in the compositions and processes which would make Carrageenan compositions more suitable for use in thermally sealed, orally administered gelatin-like capsules.

BRIEF DESCRIPTION OF THE INVENTION

The present invention describes compositions, methods of manufacturing the compositions, capsules with these compositions, and methods of manufacturing the capsules. The compositions comprise water-softenable/dispersible/soluble hydrophilic colloidal layers comprising gel films of kappa-Carrageenan (κ-carrageenan). The compositions comprise a mixture of κ-carrageenan and plasticizer. The compositions may be manufactured by mixing, blending or preferably dispersing the κ-carrageenan with the plasticizer and optionally potassium salt (or material which provides potassium for gelling the κ-carrageenan) in water. The potassium salt is at least optional because some commercially available supplies of κ-carrageenan contain natural or added (by the manufacturer) potassium cations or potassium salts. The composition may then be extruded or cast into sheet or film form and used as would conventional gelatin sheets, films or ribbons in the manufacture of capsules. In addition to the novelty of the compositions of the present invention, the fact that the κ-carrageenan compositions of the present invention could be used for manufacture of capsules in these processes was not known or apparent.

DETAILED DESCRIPTION OF THE INVENTION

The present invention relates to the manufacture of gelatin-free soft capsules employing κ-carrageenan as the main gel-forming polymer (at least 50% by weight of gel-forming material, including all gums except for those from starch derivatives such as maltodextrin, gum arabic and proteins). For example, mixtures of 50/50 κ-carrageenan/iota-carrageenan, 50/25/25 κ-carrageenan/ xanthan gum and locust bean gum, will work. Existing processing equipment for soft gelatin capsules can be used for the non-gelatin polymer composition because of the unique combination of physical properties which these compositions display, even in comparison with other natural hydrocolloids which are related to κ-carrageenan. κ-Carrageenan when dissolved in water by heating, followed by cooling, can form thermoreversible gels, optionally in the presence of additionally added cations. A film-forming gel mass is prepared by combining κ-carrageenan, water (preferably deionized water), an optional gelling salt (s), and plasticizer. Gelling salts can be salts of divalent cations such as calcium, magnesium, and barium or salts of monovalent cations such as potassium and sodium. Preferably, where a gelling salt is additionally used (in addition to the salts which may be naturally present in the commercial κ-carrageenan), a salt comprising a potassium salt, and in particular, a highly soluble potassium halide such as potassium chloride, is used. Carbohydrates, especially liquid carbohydrates, whether natural or synthetic, such as glycerin, alkylene glycols (e.g., polyethylene glycol, propylene glycol, and their mixtures or functionalized derivatives, the number present after the Tradename usually relating approximately to the molecular weight or the number of repeating units of the glycol), sorbitol (and sorbitol solution), maltitol, lactitol, xylitol, corn syrup solids, and other polyols or combinations of the above can be used as plasticizers. Preferably, a mixture of maltitol syrup and sorbitol solution is used.

It is desirable to be able to distinguish amongst the various types of gums preferred and tolerated in the practice of the present invention. Gums (hydrocolloids) that form thermoreversible gels or contribute to the formation of thermoreversible gels include, for example, κ-carrageenan, iota-carrageenan, xanthan gum, gellan gum, and mannan gums (such as locust bean gum, konjac gum, tara gum and cassia gum). The specific words used in the description of "or contribute to the formation of thermoreversible gels" are important because some of these gums, such as the mannan gums and xanthan gum, do not form thermoreversible gels by themselves, but they form thermoreversible gels with carrageenan through a synergistic effect. Gums (hydrocolloids) that do not form thermoreversible gels include dextrins (including maltodextrin), proteins, gum arabic and polyvinylpyrrolidone (e.g., Povidone™). The latter gums may simply be film formers (such as gum arabic and Povidone™) or both film formers and formers of non-thermoreversible (heat stable) gels (such as various plant proteins, for example, soy protein). The term 'thermoreversible gum' therefore refers to a gum the gel of which is thermoreversible or contributes to the formation of thermoreversible gels with κ-carrageenan.

Optionally, mannan gums (e.g., locust bean gum, konjac gum, and tara gum) which have a synergistic gelling effect with κ-carrageenan can be added to increase gel strength and elasticity. Also, part of κ-carrageenan may be substituted by iota-carrageenan (up to a maximum of 50% or 25% by weight of the κ-carrageenan) which forms "softer" and more elastic gels. Mechanical properties of carrageenan films can also be improved through a synergistic effect with added mixtures of xanthan gum (a microbial gum) and locust bean gum.

Optionally, hydrolyzed starches, such as maltodextrin (a hydrolyzed starch and an inexpensive biopolymer), are added to 1) increase solids concentration in the gel mass, 2) aid heat sealing by increasing wet film tackiness, and 3) prevent "hazing" of dried carrageenan capsules induced by the gelling salt and, if added, the mannan gums. Maltodextrin from corn starch is optionally used due to wide availability and low cost. However, dextrins from other starchy feedstocks (e.g., wheat, rice, barley, tapioca, potato, and cassava) can be used as well.

Optionally, a native or modified water-soluble or water-dispersible protein (or mixtures of proteins) derived from plant sources including, but not limited to, cereals (e.g., wheat, corn, sorghum, rice, and oat), oilseeds.(soybeans, peanuts, and cottonseed), tubers (e.g., potato), and legumes (e.g., pea and lentil) is incorporated in the gel mass to increase wet tackiness, thus improving heat-sealing properties of cast ribbons. Of course, animal proteins (e.g., whey protein, keratin, casein, egg albumen, and fish myofibrillar protein) may be used for this purpose as well. The use of animal proteins, however, would defeat one of the purposes of the use of non-animal materials in the capsule.

Preferably, the gel mass ingredients are combined in the following manner. Maltodextrin, gum arabic, and protein (if present) are dissolved. The blend of gum (carrageenan and optionally a mannan gum or a mixture of xanthan gum and locust bean gum) and the gelling salt (if present) is dispersed in the plasticizer (at about or above room temperature, with each of these non-reactive, premixing steps, being performable in any order). Then, the maltodextrin or gum arabic or protein solution is added to the gum/salt/plasticizer mixture and the gel mass is heated up to 135–210° F. under stirring. The maltodextrin may be present, for example, at above 0% such as about 10 to 500% by weight of said carrageenan (especially as a percentage of the κ-carrageenan), more preferably as about 100 to 200% by weight of said κ-carrageenan. Similar to gelatin, ribbons (sheets) can be cast from the heated gel mass for subsequent encapsulation of liquid or solid fills.

The formulations of the present invention for the preparation of essentially gelatin-free compositions may comprise, for example, 8–50% by weight of plasticizer, 0.5 to 12% by weight κ-carrageenan, and the remainder comprising water (e.g., approximately 38% to 91.5% or 95% by weight water), exclusive of consideration of other optional or preferable additives. Where the additives are the dextrins (especially maltodextrin), gum arabic and proteins, those materials may be present at levels of from 0% to about 25% or more of the composition, for between 0 and 20%, between 0.1 and 20%, between 1 and 15%, between 2 and 15% and the like. The κ-carrageenan therefore may be present as 75% or 50% by weight of all gums which form or contribute to the formation of thermoreversible gels, into which class the dextrins, gum arabic and proteins do not fit. Additional materials may be present such as colorants (e.g., dyes and pigments), flavorings, aroma agents, diluents (e.g., particulates such as calcium carbonate), minerals to enhance the benefits of the oral consumption of the capsule, antioxidants (e.g., ascorbic acid), Ultraviolet radiation absorbers to protect encapsulants, opacifying agents (e.g., titanium dioxide), dextrins (such as maltodextrin), proteins and the like. The presence of these additional ingredients may or may not be considered in the determination of the fundamental weight percentages of the plasticizer, κ-carrageenan and water. The ratio of κ-carrageenan to plasticizer may range from about 1:40 to 1:1 on a weight basis. The additional gums may comprise a minor percentage of the κ-carrageenan, as for example up to 25% or 50% by weight of the κ-carrageenan. The dextrins, as gums that do not form or contribute to the formation of thermoreversible gels, are treated differently in the tolerable amount, as described above. These additional gums or additives (whether forming thermoreversible gels or not) may be selected from mannan gums, xanthan gums, iota-carrageenan, the native or modified water-soluble or water-dispersible proteins (discussed above), gellan gums, gum arabic, polysaccharides, Povidone™ (polyvinylpyrrolidone), natural and synthetic resins and the like. It is preferred for simplicity of the composition that these additional materials be minimized or completely absent from the composition so that there is less than 50% or less than 25% of the total of these ingredients present within the composition, preferably less than 10% by weight of the total composition (comprising plasticizer, κ-carrageenan, and water) of any single ingredient or combination of ingredients, more preferably less than 5%, still more preferably less than 3% or less than 2%, and most preferably less than 1% or less than 0.5% by weight of the total composition (comprising plasticizer, κ-carrageenan, and water) of any single ingredient or combination of ingredients. The most tolerable ingredient is the iota-carrageenan. The next most tolerable ingredients comprise the natural gums such as mannan gums and xanthan gum. Mannan gums and xanthan gum, in particular, can have a beneficial effect on the system in increasing the gel strength of the capsules, reduce syneresis, and improve elasticity. Although the use of gums is tolerated or desirable (gums which do not form thermoreversible gels) or possibly particularly beneficial (thermoreversible gums) in the practice of the present invention, it is preferred that the ratio of plasticizer to the total amount of gum that forms or contributes to the formation of thermoreversible gels (if not with respect to the total of all gums) be maintained above 4:1, preferably above 5:1, and most preferably above 6:1 or above 8:1 or higher (e.g., above 10:1). It is preferred that the use of gellan gum be minimized or eliminated, with less than 0.1% by weight of the composition comprising gellan gum, preferably less than 0.05% gellan gum, and most preferably below 0.02% down to 0% of gellan gum.

A preferred method of preparation of the compositions of the present invention comprises dispersing the κ-carrageenan in the plasticizer at about room temperature or higher, adding water, heating and gelling the composition by cooling. Gelling is observed by determining particular changes in physical properties of the composition. When the composition is prepared at room temperature, it is a very viscous mass (often dough-like). Upon heating, the mass "thins out" and is converted to a clear, free-flowing liquid. The liquid may not necessarily be clear when certain optional film-forming materials are present. Materials such as proteins may impart a milky appearance or even some coloration, and, of course, if pigments or opacifying agents are added (e.g., titanium oxide), the solution would not be clear. Upon cooling (for example by casting on the surface of revolving cooled drums) the mass gels or sets, forming a freestanding ribbon (film). The composition has been found to be self-gelling, even without the addition of gelling salts (possibly because of the presence of cations in the commercial κ-carrageenan product). Gelling salts may be added, however, to accelerate the gelling, or to increase gel strength, or to control the gelling more precisely. Gelling salts (e.g., especially the potassium salts) may be present as 0% of the composition, or up to about 3% or more by weight of the composition. The amount of the salt may vary significantly because of the variation in the weight of the counterion, but is preferably within a range of 0.01 to 1% by weight of the total composition, more preferably as 0.01 to 0.5% by weight of the total composition, usually as a halide salt. Potassium citrate is also a known potassium gelling salt. The addition of the gelling salts, the percentage of additives (e.g., plasticizers, gums, iota-carrageenan, etc.) can be used to control or vary the melting point or thermal fusion point of the gel. One of the important aspects of the present invention in the use of the non-gelatin compositions is the fact that the melting or fusion temperatures of the compositions can be easily controlled. Where the encapsulant might be particularly sensitive to thermal stress or decomposition temperatures, the ability to control and especially lower the capsule processing temperatures is a useful capability.

EXAMPLES

The full scope of materials disclosed for practice of the present invention either have been prepared or may be prepared according to a general process comprising:

1. The κ-carrageenan or a blend of κ-carrageenan and iota-carrageenan/gelling salt/mannan gum/xanthan gum (if these materials are present) is dispersed, e.g., at ambient or at least slightly elevated temperature (higher temperatures, of course, usually being advantageous in the physical dissolution of most materials), in a plasticizer (or mixture of plasticizers).
2. Optional additives (e.g., the maltodextrin, gum arabic and protein) are dissolved in water (preferably at about ambient temperature, but some slight elevation or reduction in temperature may be used) to form an aqueous solution.
3. The aqueous solution is added to the κ-carrageenan/plasticizer mixture to form a working composition.
4. The working composition is heated, preferably with stirring to above 130° F. to below the boiling point of the working mixture, preferably between 135 and 210° F., more preferably between about 160 to 180° F.
5. The heated working composition can then be transferred or introduced for processing to a conventional gelatin encapsulation machine (films are formed by casting the solution on cooled rotating (e.g., metal such as steel) drums, the films are fed through a series of rollers to counter-rotating dies which form, cut and fill capsules of various sizes.

Compositions within the scope of the present invention which could be made merely by selection of the appropriate ingredients include, but are not limited to the following compositions which are expressed in percentages by weight:

Composition 1

| | |
|---|---|
| κ-carrageenan | 4% |
| Maltitol syrup | 30% |
| Sorbitol solution | 2.5% |
| Deionized water | 63.5% |

Composition 2

| | |
|---|---|
| κ-carrageenan | 4% |
| Maltitol syrup | 20% |
| Glycerin | 11% |
| Deionized water | 65% |

Composition 3

| | |
|---|---|
| κ-carrageenan | 4% |
| Potassium chloride | 0.6% |
| Polyethylene glycol 400 | 6.5% |
| Glycerin | 4.5% |
| Maltodextrin (DE 15) | 8% |
| Deionized water | 76.4% |

Composition 4

| | |
|---|---|
| κ-carrageenan | 4% |
| Maltitol syrup | 20% |
| Glycerin | 3% |
| Polyethylene glycol 400 | 8% |
| Deionized water | 65% |

Composition 5

| | |
|---|---|
| κ-carrageenan | 4% |
| Maltitol syrup | 10% |
| Sorbitol solution | 6% |
| Deionized water | 80% |

Composition 6

| | |
|---|---|
| κ-carrageenan | 4% |
| Maltodextrin (DE 15) | 5% |
| Maltodextrin (DE 18) | 5% |
| Glycerin | 4% |
| Polyethylene glycol 400 | 6% |
| Deionized water | 76% |

Composition 7

| | |
|---|---|
| κ-carrageenan | 4% |
| Potassium chloride | 0.6% |
| Glycerin | 4.5% |
| Povidone (K-15) | 5% |
| Polyethylene glycol 400 | 6.5% |
| Deionized water | 76.4% |

Composition 8

| | |
|---|---|
| κ-carrageenan | 4% |
| Maltodextrin (DE 15) | 6% |
| Glycerin | 4.5% |
| Polyethylene glycol 400 | 6.5% |
| Potassium chloride | 0.6% |
| Gum arabic | 2% |
| Deionized water | 79.4% |

Composition 9

| | |
|---|---|
| κ-carrageenan | 3.5% |
| Glycerin | 4% |
| Polyethylene glycol 400 | 4% |
| Potassium chloride | 0.5% |
| Gum arabic | 5% |
| Deionized water | 83% |

Composition 10

| | |
|---|---|
| κ-carrageenan | 3.5% |
| Maltodextrin (DE 15) | 6% |
| Glycerin | 5% |
| Polyethylene glycol 400 | 5% |
| Potassium chloride | 0.5% |
| Deionized water | 80% |

-continued

Composition 11

| | |
|---|---|
| κ-carrageenan | 3.5% |
| Maltodextrin (DE 15) | 8.5% |
| Glycerin | 6% |
| Polyethylene glycol 400 | 5% |
| Potassium chloride | 0.5% |
| Soy protein isolate | 1.5% |
| Deionized water | 75% |

Composition 12

| | |
|---|---|
| κ-carrageenan | 2% |
| iota-carrageenan | 0.5% |
| Locust bean gum | 0.2% |
| Glycerin | 1% |
| Polyethylene glycol 400 | 2% |
| Potassium chloride | 0.3% |
| Deionized water | 94% |

Composition 13

| | |
|---|---|
| κ-carrageenan | 3% |
| Locust bean gum | 0.3% |
| Glycerin | 1.5% |
| Polyethylene glycol 400 | 3% |
| Potassium chloride | 0.3% |
| Deionized water | 91.9% |

Composition 14

| | |
|---|---|
| κ-carrageenan | 1.5% |
| Locust bean gum | 0.25% |
| Xanthan gum | 0.25% |
| Glycerin | 7% |
| Potassium citrate | 0.3% |
| Deionized water | 90.7% |

Composition 15

| | |
|---|---|
| κ-carrageenan | 1.5% |
| Locust bean gum | 0.25% |
| xanthan gum | 0.25% |
| Glycerin | 3.5% |
| Polyethylene glycol 400 | 3.5% |
| Potassium citrate | 0.3% |
| Deionized water | 90.7% |

Composition 16

| | |
|---|---|
| κ-carrageenan | 3% |
| Glycerin | 1.5% |
| Potassium chloride | 0.45% |
| Polyethylene glycol 400 | 3.5% |
| Maltodextrin (DE 10) | 5% |
| Deionized water | 86.55% |

What is claimed:

1. A composition comprising:
   a) 8 to 50% by weight of a plasticizer;
   b) 0.5 to 12% by weight of κ-carrageenan; and
   c) 1 to 95% by weight water,
   wherein the κ-carrageenan comprises at least 50% by weight of all film-forming material in the composition and the weight ratio of plasticizer to κ-carrageenan is greater than 1.

2. The composition of claim 1 further comprising up to 60% by weight of a hydrolyzed starch.

3. The composition of claim 1 wherein the ratio of plasticizer to κ-carrageenan is between 4:1 and 40:1.

4. The composition of claim 1 wherein the ratio of plasticizer to κ-carrageenan is greater than 4:1.

5. The composition of claim 2 wherein the hydrolyzed starch is a dextrin.

6. The composition of claim 1 further comprising a gelling salt.

7. The composition of claim 1 further comprising less than 0.05% by weight of gellan gum.

8. The composition of claim 3 wherein mannan gum is present in the composition in an amount of less than 50% by weight of said composition.

9. The composition of claim 1 wherein said plasticizer comprises at least one ingredient selected from the group consisting of glycerin, polyalkylene glycol, sorbitol, sorbitol solution, corn syrup solids, lactitol, xylitol and maltitol.

10. The composition of claim 9 wherein said plasticizer comprises least one ingredient selected from the group consisting of glycerin, polyalkylene glycol, sorbitol solution and maltitol.

11. The composition of claim 1 further comprising a water soluble or water dispersible protein.

12. The composition of claim 1 further comprising an additive selected from the group consisting of colorants, flavorings, aroma agents, diluents, minerals, antioxidants, UV radiation absorbers, and opacifying agents.

13. The composition of claim 5 wherein the dextrin is maltodextrin, the maltodextrin being present in an amount from 0.1 to 15% by weight of the composition.

14. A process for gelling the composition of claim 1 comprising:
 a) heating the composition; and
 b) cooling the composition, thereby setting the composition into a gel.

15. The process of claim 14 further comprising adding gelling salts to the composition.

16. The process of claim 15 wherein said gelling salts comprise a potassium salt.

17. A process for gelling the composition of claim 1 into a film form comprising:
 a) heating the composition; and
 b) cooling the composition by casting the composition on the surface of revolving cooled drums, thereby gelling the composition into film.

18. A process for gelling the composition of claim 3 into a film form comprising:
 a) heating the composition; and
 b) cooling the composition by casting the composition on the surface of revolving cooled drums, thereby gelling the composition into film.

19. The process of claim 18 for forming a capsule further comprising the step of, after heating the composition, casting or extruding the composition into a film, and gelling the composition by cooling;
 associating a fill material with said film and sealing said film about said material.

20. A process for gelling the composition of claim 2 into a film form comprising:
 a) heating the composition; and
 b) cooling the composition by casting the composition on the surface of revolving cooled drums, thereby gelling the composition into film.

21. The process of claim 20 for forming a capsule further comprising the step of, after heating the composition, casting or extruding the composition into a film, and gelling the composition by cooling;
 associating a fill material with said film and sealing said film about said material.

22. The process of claim 18 further comprising adding gelling salts to the composition.

23. A capsule comprising a fill material and a capsule shell, said capsule shell comprising:
 a) a plasticizer; and
 b) carrageenan,
 wherein the carrageenan comprises at least 50% by weight of all gums forming or contributing to the formation of thermoreversible gels in the composition and the weight ratio of plasticizer to carrageenan is greater than 1.

24. The capsule of claim 23 wherein said plasticizer comprises at least one ingredient selected from the group consisting of glycerin, polyalkylene glycol, sorbitol, sorbitol solution, corn syrup solids, maltitol, xylitol, and lactitol.

25. The capsule of claim 23 wherein the capsule shell comprises less than 0.05% by weight gellan gum.

26. The capsule of claim 23 wherein the carrageenan is at least 50% by weight κ-carrageenan.

27. The capsule of claim 23 wherein said capsule shell comprises said plasticizer and carrageenan in a ratio greater than 4:1, plasticizer to carrageenan.

28. The capsule of claim 26 wherein said capsule shell comprises said plasticizer and κ-carrageenan in a ratio greater than 4:1, plasticizer to κ-carrageenan.

29. The composition of claim 1 wherein said water is present in an amount of from 38 to 98% by weight.

30. The composition of claim 24 wherein the plasticizer comprises sorbitol solution and maltitol.

31. The composition of claim 1 further including at least one non-thermoreversible gum selected from the group consisting of hydrolyzed starches, dextrins, proteins, gum arabic, and polyvinylpyrrolidone.

32. The process of claim 20 further comprising adding gelling salts to the composition.

33. The capsule shell of claim 23 further comprising a gelling salt.

34. The capsule of claim 23 further comprising a hydrolyzed starch present in an amount from 0.5 to 15% by weight of carrageenan.

35. A composition comprising:
 a) 8 to 50% by weight of a plasticizer;
 b) 0.5 to 12% by weight carrageenan;
 c) 0 to 60% by weight of at least one non-thermoreversible gum; and
 d) 0.5 to 95% by weight water,
 wherein the carrageenan comprises at least 50% by weight of all film-forming material in the composition and the weight ratio of plasticizer to carrageenan is greater than 1.

36. The process of claim 14 wherein after heating, the composition is cast or extruded into a film and the composition is gelled by cooling.

37. The process of claim 36 wherein a fill material is associated with said film and the film is sealed about said fill material.

38. The composition of claim 35 wherein the total amount of thermoreversible gums comprises at least 50% κ-carrageenan.

39. The composition of claim 38 comprising less than 0.05% by weight of gellan gum.

40. The composition of claim 38 further comprising an additional thermoreversible gum in an amount less than 50% by weight of all thermoreversible gum within the composition, the additional gum comprising mannan gum, xanthan gum, locust bean gum, or mixtures thereof.

41. The composition of claim 35 wherein the at least one non-thermoreversible gum is selected from the group consisting of hydrolyzed starches, dextrins, proteins, gum arabic, and polyvinylpyrrolidone.

42. The composition of claim 41 wherein the at least one non-thermoreversible gum is maltodextrin.

43. The composition of claim 35 wherein the plasticizer is selected from the group consisting of glycerin, alkylene glycol, sorbitol, sorbitol solution, maltitol, lactitol, xylitol, corn syrup solids, polyols and combinations thereof.

44. The composition of claim 43 wherein the plasticizer comprises maltitol and sorbitol solution.

45. The composition of claim 35 further comprising a gelling salt.

46. The composition of claim 45 wherein the gelling salt is a potassium salt.

47. The composition of claim 35 wherein the ratio of plasticizer to κ-carrageenan is greater than 4:1.

48. The composition of claim 35 further comprising an additive selected from the group consisting of colorants, flavorings, aroma agents, diluents, minerals, antioxidants, UV radiation absorbers, and opacifying agents.

49. The process of claim 17 for forming a capsule further comprising the steps of after heating the composition, casting or extruding the composition into a film, and gelling the composition by cooling:

associating a fill material with said film and sealing said film about said material.

50. A method for preparing a non-gelatin composition comprising:

a) dispersing κ-carrageenan into a plasticizer such that the weight ratio of plasticizer to κ-carrageenan is greater than 1;

b) adding an aqueous solution;

c) heating and stirring the κ-carrageenan, plasticizer, and aqueous solution mixture; and d) cooling the composition to effectively gel the mixture.

51. The method of claim 50 wherein the κ-carrageenan comprises at least 50% by weight of all film-forming material in the non-gelatin composition.

52. The method of claim 50 wherein the cooling step is accomplished by casting the mixture onto cooled rotating drums to form the composition into a film form.

53. The method of claim 50 wherein at least one additive selected from the group consisting of non-thermoreversible gums, proteins, hydrolyzed starches, dextrins, colorants, flavorings, aroma agents, diluents, minerals, antioxidants, UV radiation absorbers, and opacifying agents is dissolved in the aqueous solution prior to adding the aqueous solution to the thermoreversible gum and plasticizer mixture.

* * * * *

UNITED STATES PATENT AND TRADEMARK OFFICE
CERTIFICATE OF CORRECTION

PATENT NO. : 6,214,376 B1  
DATED : April 10, 2001  
INVENTOR(S) : Aristippos Gennadios, Ph.D.

It is certified that error appears in the above-identified patent and that said Letters Patent is hereby corrected as shown below:

Claim 10,  
Lines 6 and 7, should read -- The composition of Claim 9 wherein said plasticizer comprises sorbitol solution and maltitol. --

Signed and Sealed this

Fifth Day of March, 2002

*Attest:*

*Attesting Officer*

JAMES E. ROGAN  
*Director of the United States Patent and Trademark Office*